(12) United States Patent
Beachy et al.

(10) Patent No.: US 7,744,857 B2
(45) Date of Patent: Jun. 29, 2010

(54) ANTIPERSPIRANT COMPOSITIONS

(75) Inventors: Denise Marie Beachy, Midland, MI (US); Kevin Ronald Franklin, Wirral (GB)

(73) Assignee: Unilever Home & Personal Care USA a division of Conopco, Inc., Chicago, IL (US)

( * ) Notice: Subject to any disclaimer, the term of this patent is extended or adjusted under 35 U.S.C. 154(b) by 1287 days.

(21) Appl. No.: 10/775,510

(22) Filed: Feb. 10, 2004

(65) Prior Publication Data

US 2004/0185019 A1 Sep. 23, 2004

(30) Foreign Application Priority Data

Feb. 11, 2003 (GB) .................. 0303104.4

(51) Int. Cl.
| | |
|---|---|
| *A61K 8/00* | (2006.01) |
| *A61K 8/26* | (2006.01) |
| *A61K 8/28* | (2006.01) |
| *A61K 8/58* | (2006.01) |
| *A61K 9/00* | (2006.01) |
| *A61K 8/02* | (2006.01) |
| *A61Q 15/00* | (2006.01) |
| *A61Q 5/12* | (2006.01) |

(52) U.S. Cl. .................. 424/65; 424/66; 424/68; 424/70.12; 424/70.121; 424/400; 424/401

(58) Field of Classification Search ............ 424/65, 424/66, 68, 70.12, 70.121, 400, 401
See application file for complete search history.

(56) References Cited

U.S. PATENT DOCUMENTS

| | | | | |
|---|---|---|---|---|
| 3,969,087 | A | 7/1976 | Saito et al. ........... 44/7 C |
| 5,500,209 | A | 3/1996 | Ross et al. ........... 424/66 |
| 5,541,278 | A * | 7/1996 | Raleigh et al. ......... 528/29 |
| 5,840,287 | A | 11/1998 | Guskey et al. ......... 424/65 |
| 6,251,377 | B1 | 6/2001 | Franklin .............. 424/65 |
| 6,395,704 | B1 | 5/2002 | Branlard et al. ........ 512/1 |
| 6,410,003 | B1 | 6/2002 | Bhatia et al. .......... 424/65 |
| 6,437,163 | B1 | 8/2002 | Branlard et al. ....... 556/450 |
| 6,451,295 | B1 | 9/2002 | Cai et al. ............ 424/65 |
| 6,503,492 | B2 * | 1/2003 | McGlone et al. ....... 424/65 |
| 2003/0162929 | A1 * | 8/2003 | Verbruggen et al. ..... 528/10 |
| 2004/0213748 | A1 * | 10/2004 | Chuah et al. ......... 424/65 |

FOREIGN PATENT DOCUMENTS

| | | |
|---|---|---|
| EP | 0 006 739 | 1/1980 |
| EP | 1 072 627 | 1/2001 |
| GB | 201164 | 8/2004 |
| WO | 94/24993 | 11/1994 |
| WO | 97/36573 | 10/1997 |
| WO | 98/27954 | 7/1998 |
| WO | 99/52965 | 10/1999 |
| WO | 00/27348 | 5/2000 |
| WO | WO 00/27348 * | 5/2000 |
| WO | 00/61096 | 10/2000 |
| WO | 01/97768 | 12/2001 |
| WO | 03/005976 | 1/2003 |
| WO | 03/005977 | 1/2003 |
| WO | WO 03/005977 * | 1/2003 |
| WO | 03/059307 | 7/2003 |
| WO | 2005/000856 | 1/2005 |
| WO | WO 2005/000856 * | 1/2005 |

OTHER PUBLICATIONS

U.S. Appl. No. 11/316,596, filed Dec. 2004, Cropper et al.*
GB Search Report in a GB Application GB 0303104.4.
PCT International Search Report in a PCT application PCT/GB 2004/000528.

* cited by examiner

*Primary Examiner*—Johann R Richter
*Assistant Examiner*—Mei-Ping Chui
(74) *Attorney, Agent, or Firm*—Karen E. Klumas

(57) ABSTRACT

Antiperspirant compositions containing suspended antiperspirant actives in a water-immiscible carrier leave visible deposits on skin or clothing unless the actives are masked. The carrier mixture in compositions herein comprise an alkylsiloxane which is substituted by a group $R^4$ of formula $-CH_2-C(Ph)(R^B)-R^5-Ph$ in which $R^B$ represents H or methyl and $R^5$ represents an alkylene group containing 0 to 3 carbons, and in which the proportion of aryl carbon atoms is at least 60% of all carbon atoms in the molecule. Preferably, the substituent comprises diphenylethyl. Optionally, the siloxane can be capped by the residue of a substituted vinyl group other than $R^4$ or an alkyl, cycloalkyl or aralkyl alcohol.

23 Claims, No Drawings

ANTIPERSPIRANT COMPOSITIONS

The present invention relates to antiperspirant compositions and in particular to anhydrous compositions containing a particulate antiperspirant active suspended in a carrier fluid.

TECHNICAL FIELD

Background of the Invention

Antiperspirant compositions are available to consumers in a variety of different applicators, and in a variety of different product forms. These can include powders, liquids, creams, gels or soft solids and sticks. Powders can be sprayed or applied by a sponge, liquids can be sprayed or from a wipe or a roll-on contact applicator, creams, gels and soft solids from a dispenser in which the composition is expelled from a reservoir onto a domed applicator surface through apertures in it and sticks are normally applied from an open-ended barrel. Consumers vary from country to country in their preferences. In order to satisfy the market place widely, it is accordingly desirable for a manufacturer of antiperspirant compositions to be able to provide one or more composition for each applicator.

Compositions can also be classified in accordance with the chemical nature of a carrier fluid. Some compositions contain a distinct phase comprising water and/or a highly polar, hydrophylic solvent such as propylene glycol. This phase can dissolve the antiperspirant active and the resultant product is usually a liquid or gel, optionally in the form of an emulsion. Other compositions, however, are anhydrous and comprise an apolar, water-immiscible liquid in which a particulate antiperspirant active is suspended. Such anhydrous compositions can be in the form of liquids, soft solids or sticks, depending on the extent to which the carrier liquid has been thickened or solidified.

One of the attributes of antiperspirant compositions to which a significant proportion of consumers pays considerable attention is the appearance of the product. There are three occasions at which consumers consider appearance, to a greater or lesser extent. These comprise the appearance of the product in the dispenser, the appearance of the product when dispensed onto the body, typically the axilla, and finally the appearance of the product on any clothing which may come into contact with the composition, for example if it is brushed off the skin surface onto a black dress, skirt or trousers. The appearance of anhydrous antiperspirant compositions is significantly affected by the comparative refractive index of the carrier fluid (mixture) and of the suspended antiperspirant active and/or any other particulate materials that are incorporated and/or by the choice of thickener, gellant or structurant that is employed to thicken or solidify the carrier. A mismatch between two or more refractive indexes causes the product to be opaque and appear white on skin or clothing. This is not liked by many consumers.

One class of carrier fluids which has been favoured by manufacturers of antiperspirant compositions comprises hydrocarbyl substituted siloxanes or cyclosiloxanes, such as dimethicones or cyclodimethicones. Whilst such carrier liquids have many attractive characteristics, they tend to have a comparatively low refractive index in relation to particulate aluminium or aluminium/zirconium antiperspirant actives. As a consequence, compositions containing a preponderance of such silicone fluids tend to be opaque and/or appear white when applied onto skin.

It is a desideratum of antiperspirant manufacturers to be able to formulate compositions which suffer from no greater than low visible deposits, by comparison with the extent of visible deposits from conventional wax-structured antiperspirant sticks. Formulations that promise low visible deposits are taking a significant market share. It is also desirable to be able to produce formulations which are clear, but using water-immiscible carriers having their attendant sensory properties.

Various different means have been suggested for countering the formation of visible deposits from antiperspirant compositions employing cyclomethicone carrier fluids. Substitute carrier fluids can be contemplated for a significant fraction or all of the silicone fluids, but that does not address the question of how to retain the use of silicone fluids. The refractive index of the antiperspirant active particulates can be altered, for example by control of their residual water of hydration. That is of limited value, because the change in refractive index that can be effected is quite small in practice. Thirdly, the refractive index of silicone fluids can be increased by increasing the density of their aryl substituents relative to the commonly employed short chain alkyl, siloxanes, such as cyclomethicones. It is inherently desirable for an antiperspirant manufacturer to have the option of employing silicone fluids having a high refractive index such as at least 1.54, because this gives him considerable flexibility in creating carrier mixtures for suspending antiperspirant solids with a reasonable or very close refractive index matching. Commonly, materials with such a refractive index are obtainable with a high aryl density, but those on the market can be obtained by substituting a significant fraction of the methyl groups in a di or polymethicone substrate by phenyl groups.

Although this third route can be effective to some extent, it becomes progressively difficult and expensive to carry out the substitution reaction for an increasing proportion of aryl substituents, and in particular when greater than one aryl substituent per silicon atom is desired. Without being bound by any single theory, aryl groups are comparatively large so that substitution reactions can suffer from steric hindrance, and the presence of an existing aryl substituent can increase the barrier activation energy for a subsequent substitution. Accordingly, the production of phenyl substituted siloxanes having a high refractive index, on a bulk scale, can entail very long reaction times, and/or precise or extreme operating conditions. Such processes can be inherently expensive to operate and control, so that the resultant product is intrinsically expensive to produce. Mass market antiperspirant compositions are price sensitive so that phenyl substituted siloxanes produced hitherto with high aryl density are not affordable for incorporation as the carrier or main carrier liquid in such compositions compared with the low refractive index cyclomethicones. That is because a carrier fluid represents a substantial fraction of the composition, commonly at least 30% of its weight and often from 40 to 70% of its weight. As far as antiperspirant manufacturers are concerned, they still have a hitherto unsatisfied want for a silicone fluid having an acceptably high aryl density that is made by a route that is more affordable.

There is described in WO 99/52965 (U.S. Pat. No. 6,395, 704 and U.S. Pat. No. 6,437,163) a process for making silicone fluids employing a hydrosilation reaction with a vinyl reagent. This patent family contemplates the preparation of a wide range siloxane fluids. The minimum number of vinyl residues Z is 1 for 6 silicon atoms, Z being a polar or polarisable radical and the remainder of substituents on the silicon atoms being alkyl groups containing from 1 up to 8 carbons. The text is seeking to identify fluids for use with perfumes, by meeting a number of Hansen solubility parameters. Although the perfumes and siloxane fluids are contemplated for use in cosmetic compositions, including antiperspirant compositions, the patents do not consider the problem of refractive index matching of liquid carrier and suspended particulate material, and unsurprisingly give no teaching on how to solve that problem.

A very large number of possibilities were suggested in said WO 99/52965 for Z including derivatives of saturated or unsaturated $C_2$-$C_{10}$ multivalent aliphatic groups, such derivatives including esters or primary or secondary amides or carboxylic acids, saturated or unsaturated C6-C20 haloaliphatic radicals or halocycloaliphatic radicals, or aryl radicals. Amongst the list of radicals that are named are aryl radicals, but the only one that is exemplified in a working example employs styrene. The siloxanes made with that reactant would not enjoy a high enough refractive index. Amongst other reactants named without supportive data, one material listed without prominence or preference is the residue of α-methylstyrene dimer. Without the benefit of hindsight, there is no reason for singling out merely one possible derivative from the very many derivatives similarly disclosed in the patent text, still less suitably selecting the remaining substituents appropriately in conjunction with that selected derivative to solve a problem concerning the refractive index of the composition constituents not contemplated by the patentee.

OBJECT OF THE INVENTION

It is an object of the present invention to ameliorate or overcome one or more of the problems identified above.

SUMMARY OF THE INVENTION

According to the present invention there is provided an antiperspirant composition comprising:
a) from 0.5 to 50% by weight of a particulate aluminium and/or aluminium/zirconium antiperspirant active;
b) from 30 to 95% by weight of a water-immiscible carrier fluid or mixture of fluids;
c) optionally up to 40% by weight of a thickener, gellant or structurant for the carrier fluid;
in which the carrier fluid comprises an aryl substituted siloxane which satisfies the general formula 1

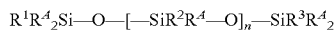

in which
n represents an average number of from 0 to 2
$R^1$ $R^2$ and $R^3$, which may be the same as or different from each other, each represents a group $R^4$ of formula

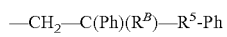

in which $R^B$ represents H or —$CH_3$ and $R^5$ represents an alkylene group containing from 0 to 3 carbon atoms, optionally branched
and not more than one of $R^1$ $R^2$ and $R^3$ can optionally represent $R^C$, namely the hydrogenated residue of a substituted vinyl group other than $R^4$ or the residue of an aliphatic alcohol, cycloaliphatic alcohol or aralkyl alcohol
and $R^A$ represents a $C_1$ to $C_4$ alkyl group provided that at least 60% of carbon atoms in total in substituents $R^A$ $R^4$ and $R^C$ are present in aryl groups.

Herein, phenyl-substituted siloxanes satisfying general formula 1 are sometimes referred to as invention siloxanes. The siloxane fluids described in the summary of the invention above have a high density of phenyl or other aryl groups, by virtue of the essential inclusion of substituents of formula $R^4$ and the limitation of the proportion of carbon atoms that can be present in alkyl groups in the aryl-substituted siloxane molecule—no more than 40% of all carbon atoms. As a direct consequence of such limitations, the resultant siloxane fluid has a high refractive index, typically of at least 1.54, thereby rendering them especially useful in a carrier fluid for particulate antiperspirant actives to assist refractive index matching, even for aluminium/zirconium actives, and can do so in a manner that is more affordable than using prior produced siloxanes having high phenyl density.

DETAILED DESCRIPTION OF THE INVENTION AND PREFERRED EMBODIMENTS

The present invention comprises compositions containing a particulate antiperspirant salt suspended in a water-immiscible carrier fluid comprising a siloxane that is substituted by the residue of hydrogenated vinyl groups $R^1$ $R^2$ and $R^3$ containing two phenyl substituents, which sometimes herein may be called invention siloxanes for convenience. Although the refractive index of the siloxane varies according to its actual constitution, they usually fall within the range of from 1.54 to 1.58, a range that is especially suitable for matching with antiperspirant active particulates.

The compositions employ a linear siloxane containing from 2 to 4 silicon atoms. Nominally, each siloxane unit in the invention siloxanes is substituted by the hydrogenated residue of a substituted vinyl groups, respectively $R^1$ $R^2$ and $R^3$, and optionally one of them by an alternative $R^C$, provided that the criteria is met that at least 60% of all the carbon atoms in the phenyl-substituted siloxane molecule are present in aryl groups. Commonly, the proportion of such aryl carbon atoms in such siloxane molecules is not higher than 80%, and in many desirable embodiments is between 70 and 77% of the total number of carbon atoms in the aryl-substituted siloxane.

In the group $R^4$, in many desirable embodiments, $R^B$ represents H and $R^5$ contains 0 carbons atoms, so that the resultant group is diphenylethyl. It will be recognised that the resultant siloxanes are especially desirable because, in general, they have a comparatively high refractive index, in many instances in the region of at least 1.55. In the absence of a capper, or indeed by suitable choice of capper, if one be desired, such diphenylethyl substituted siloxanes can have a refractive index of about 1.56 to 1.575. When $R^4$ represents diphenylethyl, n is often not greater than 1, and in many instances is from 0 to 0.5. Such selections represent a preferred combination of high refractive index and comparatively low viscosity for the siloxane fluid.

In other embodiments, $R^5$ in group $R^4$ represents an alkylene group containing 2 or 3 carbons, such as —($CH_2$)—($CH_2$)— or —($CH_2$)—($CH(CH_3)$)—. When $R^B$ also represents a methyl group, a suitable example comprises the hydrogenated residue from α-methyl styrene dimer. Siloxanes made using α-methyl styrene dimer as reagent advantageously have little detectable odour from any residual reactant, which is of practical benefit in cosmetic products. Preferably, when $R^B$ is such a residue, n is preferably 0.5 to 1.5, such as in the region of 1.0+/−0.2 on average.

In the "invention" siloxanes employed herein, $R^A$ is a short chain alkyl group, conveniently containing up to 4 carbons, though subject to the limiting proportion of 40% of carbon atoms in other than aryl groups. The invention is described herein particularly with respect to the use of siloxanes in which such substituents $R^A$ are each methyl groups. It is a particularly preferred that at least 75% of $R^A$, and especially substantially all $R^A$ groups are methyl, because this can maximise the refractive index of the resultant siloxane.

Herein, the siloxane molecule can be capped with a limited fraction of $R^C$, an substituted ethyl group that is not $R^4$, or with the residue of an aliphatic, cycloaliphatic or aralkyl alcohol, provided that the resultant molecule still contains at least 60% aryl carbons. Capping is particularly suitable if $R^4$ represents diphenylethyl, in which case it could also be capped using α-methyl styrene dimer. Usually not more than 20% of the total occurrences of $R^1$, $R^2$ and $R^3$ are other than $R^4$, ie by a capping group and often not more than 15%, such as from 10 to 15%. The employment of such a minor fraction of an alternative group $R^C$ can minimise the extent to which the invention siloxane has a residual content of diphenylethylene or can vary the viscosity of products made using α methyl styrene dimer. This can be achieved by employing a substoichiometric amount of the major reactant eg diphenylethylene in an initial reaction stage and employing the alternative minor reactant in a second stage. By employing only a minor fraction of the alternative substituent, the impact of such a substituent on the refractive index of the siloxane can be minimised, or at least kept within a tolerable change.

Suitable alternative capping reagents are particularly preferably liquid under use conditions and include styrene, benzyl alcohol cyclohexanol, branched alkyl fatty alcohols and allyloxyethanol. Advantageously, the selection of a residue from a reactant that itself comprises an aryl ring can enable the phenyl density to be maintained to a greater extent than if the reactant lacks an aryl substituent. It will also be recognised that where the major reactant is diphenylethylene, the capping reactant can comprise α-methyl styrene dimer.

Very desirably, in the invention siloxanes, $R^1$ $R^2$ and $R^3$ may be diphenylethyl, but that is not essential. Such siloxanes can also offer a practical processing benefit. For the manufacture of products in which the carrier fluid is structured, so that it is solidified, possibly flowing when subjected to hand pressure, it is conventional for the structurant (gellant) to be melted or otherwise form a single phase with the carrier liquid at an elevated temperature and for the antiperspirant composition to solidify on cooling. If there is only a narrow window between the temperature at which all the ingredients are incorporated into the composition and its solidification temperature, it is relatively difficult on a plant scale to avoid premature solidification, such as in the pipework from the composition production unit and the composition filling station. Advantageously, the choice of diphenylethyl substituted siloxanes fluids as described herein enables the composition to enjoy a comparatively low solidification temperature and a wide processing temperature window compared with commercially available phenylated siloxane fluids of similar refractive index.

In the formula for the invention siloxane employed herein, the molecule can comprise simply two terminal siloxanes of formula R(Me)$_2$Si linked by an oxygen atom, or can contain up to average n=2 interposed units of formula —[SiR$^2$R$^4$—O]— In many instances, n is a number average of not higher than 1.5. In some embodiments, and especially where R represents a diphenylethyl residue, n is in the region of 0.

It will be recognised that the viscosity of the invention siloxanes can be controlled by varying the chemical nature and proportion of the alternative substituted ethyl group, an increased proportion tending to increase the viscosity. Likewise, an increase in the length of the siloxane molecule tends to increase viscosity. Accordingly, it is possible to obtain formulations with a carrier fluid having a high refractive index and a range of viscosities, by varying the proportions of the component invention siloxanes, for example to control the dispensing of liquid formulations.

Although it is at the discretion of the manufacturer as to what proportion of the carrier mixture is provided by invention siloxane, the benefit increases as the proportion increases or the absolute proportion of the invention siloxane in the composition increases when compared with the incorporation of previous commercial siloxanes of similar refractive index. Desirably, at least 30 or 35%, preferably at least 50% and in many embodiments more preferably at least 60% by weight of the water-immiscible carrier fluid comprises the invention siloxanes. In many instances, the proportion of invention siloxanes in the carrier fluid mixture is not greater than 95%, desirably up to 90% and in a number of preferred embodiments up to 85% of the weight of the fluid mixture.

In various embodiments of the invention, the invention siloxanes can be employed in a sufficient proportion of the carrier fluids to act as a masking oil for suspended particulate antiperspirant actives. In such embodiments, the extent of masking increases as the proportion of the invention siloxanes increases in the carrier fluid mixture, up to the point at which the RI of the mixture matches that of the suspended particulate material that it is masking. Commonly, the proportion of a masking oil in a carrier fluid is from 10 to 30% by weight and particularly from 15% to 25%.

The invention siloxanes herein can be made by a hydrosilylation reaction in which a corresponding substrate satisfying the formula 2 below when $R^4$ is methyl, and mutatis mutandis for other $R^A$ alkyl groups.

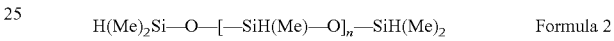  Formula 2 in which n is as defined herein above is reacted with a substituted vinyl reactant, in the presence of a hydrosilation catalyst such as inorganic supported platinum or palladium catalysts, e.g. on divided carbon, in an amount of less than 5% by weight of the substrate in the presence of hydrogen at an elevated temperature, commonly from 40 to 200° C. and at a pressure often from ambient up to an elevated pressure of 2500 mPa. If in the intended product, the substituted vinyl reactant is solely diphenylethylene or α-methylstyrene dimer, then it is desirable to employ a slight excess over stoichiometry. If however, a minor fraction of the reactant comprises a different reactant, such as α-methylstyrene dimer or other listed alternative reactant $R^C$ when the major fraction of the substituent $R^4$ derives from diphenylethylene, it is more convenient to conduct the reaction in two stages, the major reactant being employed in the first stage at the desired substoichiometric amount, and in a subsequent reaction, the intermediate product is capped by reaction with a slight excess of the minor reactant compared with the residual number of SiH moieties present. It is convenient to monitor the reaction, for example by periodic sampling and glc analysis and maintain reaction conditions until the SiH moieties have been reacted.

The balance of the carrier fluid can be provided by alternative water-immiscible liquids, including volatile and/or non-volatile silicone liquids, volatile and/or non-volatile hydrocarbon liquids, liquid fatty alcohols or benzyl alcohol, liquid esters of fatty alcohols, and liquid ether terminated polyalkylene glycols. Herein liquid indicates that the material has a melting point of not higher than 20° C. Preferably, such additional water-immiscible carrier materials herein have a boiling point of at least 75° C. and particularly in the range of up to 150° C.

Volatile silicones are usually selected from cyclic polysiloxanes containing from 3 to 8 dialkylsiloxane groups, (cyclomethicones) especially dimethylsiloxane groups and particularly 4 and/or 5 dimethylsiloxane groups (tetra- and penta-cyclomethicones). Other useful volatile silicones can comprise linear polysiloxanes, usually containing up to 8 and preferably 4 or 5 dialkylsiloxane groups, including terminal groups, commonly called dimethicones when both alkyl substituents are methyl. Low molecular weight liquid hydrocarbons that are volatile can comprise paraffin oils, often isoparaffin oils. Incorporation of such volatile materials as a fraction of the carrier fluid can assist in the matching of the refractive index of the suspended antiperspirant active and the carrier fluid. The refractive index of the volatile silicones is commonly in the region of 1.4 and of volatile hydrocarbons is around 1.42/1.43. Their presence can increase the rate of evaporation of carrier fluid from the skin after topical application.

Non-volatile silicone oils which can be employed in conjunction with the invention siloxanes can comprise linear alkylarylpolysiloxanes containing up to 4 or 5 siloxane silicon atoms, such as methylphenylsiloxanes often in which there is from 0.5 to 1.2 phenyl substituent per methyl substituent, as for example in DC556™ or DC704™ available from Dow Corning, Inc. Such materials have an intermediate or high refractive index, though for the reasons indicated hereinbefore the extent of the use with high refractive index is jeopardised by their cost. Other non-volatile silicones comprise intermediate and higher molecular weight linear dimethicones that are liquid at 20° C., such as members of the DC200™ series of silicone oils having a viscosity of at least 1 mPa·s, available from Dow Corning, Inc., and having a relatively low refractive index.

Non-volatile hydrocarbon oils, which often contain on average between 20 and 40 carbon atoms, include mineral oil and hydrogenated polydecene. Such materials have an intermediate refractive index in the region of 1.45 to 1.475.

Liquid fatty alcohols are normally branched chain alcohols containing from 12 to 25 carbons and several such desirable alcohols contain from 16 to 20 carbons, including isostearyl alcohol and octyl-decylalcohol. They have an intermediate refractive index in the region of 1.45 to 1.46. In conjunction with certain structurants, such as cyclodipeptide esters, their use can not only assist in refractive index matching, but can also aid the avoidance of premature gelation of a soft solid or stick composition as the composition cools prior to being filled into its dispensing container.

In some particularly desirable compositions, the carrier fluid mixture comprises from 20% to 35% by weight of a liquid fatty alcohol and/or a non-volatile hydrocarbon and/or alkyl benzoate, and particularly from 23 to 30% by weight. Such mixtures are especially well suited for employment in conjunction with a suspended activated antiperspirant active having an intermediate refractive index in the region of 1.53. Different proportions of the carrier constituents can be calculated to achieve a desired extent of RI matching, should the suspended antiperspirant active have a higher or lower refractive index.

In most of the formulations herein, the refractive index of the carrier fluid mixture and the antiperspirant active solid is matched at least loosely, such as with in 0.05 units or comparatively closely, such as within 0.005 units. In some embodiments, the matching is +/−0.001 units.

The antiperspirant active employed herein comprises an astringent aluminium or zirconium salt. The proportion of antiperspirant active present in the composition according to the invention is often from 1-40% by weight of the composition, preferably at least 5% by weight and more preferably 15-30% by weight of a composition not intended for mixture with a propellant, or 15 to 50% in a base composition intended for mixture with a propellant that may be employed in order to make an aerosol composition.

Classes of suitable actives include aluminium salts, zirconium salts, aluminium and/or zirconium complexes, for example aluminium halides, aluminium hydroxy halides, zirconyl oxyhalides, zirconyl hydroxyhalides, and mixtures thereof. However, it is desirable to employ basic aluminium and/or zirconium salts, as such or complexed, suitable complexants including aminoacids, including particularly glycine, and especially salts in which the halide is chloride. Specific examples of preferred salts include activated aluminium chlorohydrate, aluminium chlorohydrate, aluminium pentachlorohydrate and aluminium zirconium chlorohydrate. Useful zirconium salts include zirconium hydroxy-chloride and zirconium oxychloride. Various generally used actives will be known to those skilled in the art. Preferred antiperspirant actives include ZAG (Zirconium Aluminium Glycine), AAZG (Activated Aluminium Zirconium Glycine), and AACH (Activated Aluminium Chorohydrate) activation for example as described in EP6739. In practice, the choice of antiperspirant employed will also take into local regulations, so that in many countries, aerosol formulations employ aluminium salts.

The antiperspirant active is present in particulate form suspended in the carrier fluid. The particle size of the antiperspirant salt is at the discretion of the producer of the composition, though in practice, it will normally comprise particles that are mainly in the diameter range of from 0.1 to 100 μM, and in many instances providing a weight average particle diameter of from 10 to 60 μM. The particle size and distribution will commonly also take into account the applicator in accordance with principles known to the skilled person.

The refractive index of the antiperspirant active normally falls within the range of 1.46 to 1.565. Actives containing solely aluminium species tending to occupy the middle and lower end of the range, particularly up to about 1.53. Thus, aluminium chlorohydrate, for example, as made, often has a refractive index of about 1.48 to about 1.50 and activated aluminium chlorohydrate at about 1.51 to about 1.53. Actives containing zirconium, as made, occupy the middle and upper end of the range, particularly from about 1.52 to 1.565 and especially from about 1.53 upwards, for example glycine complexes of aluminium/zirconium chlorohydrates. The residual water content of the antiperspirant active is a contributing factor to its eventual refractive index, increasing water reducing the refractive index. Consequently, within a range of possibly 0.02 to 0.03 units, the refractive index of an active can be modified by controlling the drying of the active or by a post manufacture treatment in accordance with published procedures, in which the active is contacted with a limited proportion of water, or if desired by a polar liquid, such as a dihydric alcohol (eg ethylene or propylene glycol) for example in an amount of up to 5% by weight of the active.

It will be recognised that the inherent high refractive index of the invention silicone fluids enables them to be employed in conjunction with any aluminium or aluminium/zirconium active and still attain formulation clarity. The range is particularly great for the siloxanes substituted by predominantly diphenylethyl as $R^4$.

The carrier fluid or mixture of fluids can be thickened or solidified (structured) employing organic or inorganic thickeners, gellants or structurants known to a skilled man in the art for the respective class of carrier materials, and in the amounts needed to achieve the extent of thickening, gelling or structuring desired by the producer. The amount of such thickener, gellant or thickener is usually selected within the range of from 0.1 to 30% by weight of the composition, depending on the nature of the final formulation which the producer wishes to make. Such formulations can comprise liquids of low viscosity, such as from 500 to 5000 mPa·s, which can be employed in roll on or pump-spray or squeeze-spray dispensers. Other thickened or gelled compositions comprise creams or soft solids, which typically have a hardness of from 0.003 to 0.5 N/mm$^2$, as measured by sphere indentation and frequently, from 0.005 up to 0.1 N/mm$^2$, which compositions flow when subjected to mild pressure (1 to 5 psig) and are commonly dispensed through an apertured dome. Yet other compositions are in the form of sticks which retain their physical integrity and shape when subjected to similar low pressure, usually have a hardness of greater than 0.5 N/mm$^2$, as measured by sphere indentation and are commonly dispensed through the open end of a barrel container.

It will be recognised that the choice of thickener or gellant may take into account any impact on the appearance of the product. Consequently, it is often desirable to employ oil-soluble organic agents for that purpose in order to retain at least low visible residues on the skin and possibly translucency on an applicator surface rather than insoluble inorganic particulate materials that would not be refractive index matched with the carrier fluid.

Three classes of thickeners or solidifying agents comprise polymers, which may be copolymers with polysiloxanes, non-polymeric agents which form fibres and waxes.

Suitable thickening polymers can be selected from polysaccharides esterified with a fatty acid of which one excellent example comprises dextrin palmitate: polyamides as discussed in U.S. Pat. No. 5,500,209, such as the product available under the trade name Versamid™ that can be derived from hexamethylene diamine and adipic acid; alkylene/arylene block copolymers, for example styrene and ethylene, propylene and/or butylene block copolymers eg SEBS block copolymers, many of which are available under the trade name Kraton™. The concentration of such polymers in the water-immiscible liquid is often selected in the range of from 1 to 20%, depending on the extent of thickening or structuring required, and the effectiveness of the chosen polymer in the liquid/mixture.

One class of gellant which is desirable for some compositions by virtue of its long standing proven capability to produce firm solids and more recently in making soft solids, comprises waxes. However, the inclusion of waxes reduces the extent to which light can be transmitted through them, so that their use is of particular benefit in making opaque compositions in bulk which can exhibit low visible residues on application onto the skin.

Herein, the term wax is employed to encompass not only materials of natural origin that are solid with a waxy feel and water-insoluble at 30-40° C., but melt at a somewhat higher temperature, typically between 50 and 95° C., such as beeswax, candelilla or carnauba wax, but also materials having similar properties. Such other waxes include hydrocarbon waxes, eg paraffin wax, mineral wax and microcrystalline wax; synthetic waxes, such as polyethylene of 2000 to 10000 daltons; waxy derivatives or waxy components of natural waxes, such as ester components, either extracted or synthesised, solid ester derivatives of glyceryl or glycol, typically with linear saturated fatty acids, usually containing a significant fraction of $C_{16-22}$ acid residues, which may be synthesised or obtained by hydrogenating the corresponding natural oil; petroleum waxes, waxy silicone polymers containing alkyl substituents of at least C10 chain length; and, importantly, waxy fatty alcohols, that normally are linear and often contain from 14 to 24 carbons, such as stearyl alcohol, cetyl alcohol and/or behenyl alcohol.

A further class of structurants for water-immiscible liquids that are employable herein, in accordance with their disclosure in patent literature relating to the preparation of antiperspirant formulations in soft solid or firm stick form include polymeric gellants. Examples of oil-soluble polyamides or amide/silicone copolymers are described in U.S. Pat. No. 6,451,295 or WO 9736573.

Yet other gellants include fibre-forming gellants, including hydroxystearic acid, such as 12-hydroxystearic acid, or ester or amide derivatives thereof, N-acyl amino acid amides and esters described in U.S. Pat. No. 3,969,087, such as, in particular, N-Lauroyl-L-glutamic acid di-n-butylamide; amide derivatives as set forth in WO 98/27954 notably alkyl N,N' dialkyl succinamides; cyclic ester derivatives of aspartame; lanosterol, as set forth in U.S. Pat. No. 6,251,377; amido derivatives of cyclohexane as set forth in U.S. Pat. No. 6,410,003; a combination of a sterol and a sterol ester as set forth in WO 00/61096, eg γ-oryzanol and β-sitosterol; and fatty acid esters of cellobiose, such as in particular a product containing predominantly cellobiose octanonanoate and a minor fraction of cellobiose heptanonanoate. Fibre-forming gellants for siloxane carrier liquids are particularly suited to the formation of solid antiperspirant products that are translucent or clear in pack.

Mixtures of materials within each class of gellant/structurant con be employed, as can mixtures of materials from two or each of the classes.

If the invention composition comprises an aerosol composition, it contains a propellant in addition to a base composition as described herein above, commonly in a weight ratio of from 95:5 to 40:60, and in many formulations, the weight ratio is from 90:10 to 50:50. The propellant is conveniently a low boiling point material, typically boiling below −5° C., for example an alkane such as propane, butane or isobutane, and possibly containing a fraction of pentane or isopentane, or a hydrofluorocarbon or fluorocarbon of similar carbon content. During filling of the aerosol canister, the propellant gas is liquified by virtue of the elevated pressure that is generated therein.

The invention compositions herein can comprise one or more optional constituents which have hither to been incorporated or proposed for incorporation in antiperspirant compositions. Such optional constituents may be liquid or solid, and normally comprise in total not more than 10% by weight of the composition. Such optional constituents can comprise sensory modifiers, such as finely divided polyethylene, such as in an amount of up to 5% by weight; fragrance, including, if desired deoperfumes, often in an amount of up to 4%, eg 0.3 to 2% by weight, colourants; skin cooling agents such as menthol; wash-off agents such as non-ionic surfactants.

When seeking to make translucent or clear products employing the invention siloxanes described herein, it is preferable to avoid incorporating any particulate material such as talc or particulate silica having a refractive index different from that of the antiperspirant active. Likewise, for translucent or clear products it is desirable to avoid wax structurants which similarly have a refractive index that is different from the antiperspirant active, thereby avoiding the problem of seeking to match simultaneously a carrier with two different refractive indexes.

The invention compositions can be made by the skilled man using methods known in the antiperspirant industry or described in published literature for the preparation of antiperspirant roll on, squeeze or pump spray cream or soft solid or firm stick compositions. Likewise, the invention compositions can be dispensed using the appropriate dispensers for such antiperspirant roll on, squeeze or pump spray cream or soft solid or firm stick compositions as have been employed or described in published literature.

Having described the invention in general terms, specific embodiments thereof will now be described more fully by way of example only.

In the examples, the new siloxane materials used were as shown in Table 1 below:—

TABLE 1

| | | Siloxane | | | | |
|---|---|---|---|---|---|---|
| | | | $R^4$ | | $R^C$ | Refractive |
| | n | $R^4$ | % | group | % | reactant | Index |
| NS124 | 0 | $CH_3$ | 100 | DPE | 0 | | 1.568. |
| NS144 | 1.3 | $CH_3$ | 100 | DPE | 0 | | 1.574 |
| NS053 | 0 | $CH_3$ | 85 | DPE | 15 | AMSD | 1.556 |
| NS078 | 0 | $CH_3$ | 85 | DPE | 15 | AMSD | 1.561 |
| NS065 | 0 | $CH_3$ | 85 | DPE | 15 | AOE | 1.555 |
| NS068 | 0 | $CH_3$ | 85 | DPE | 15 | BA | 1.558 |
| NS070 | 0 | $CH_3$ | 100 | AMSD | 0 | | 1.542 |
| NS050 | 1 | $CH_3$ | 100 | AMSD | 0 | | 1.546 |

In Table 1, DPE represent diphenylethyl and AMSD represents as appropriate α-methylstyrene dimer or its hydrogenated residue as is appropriate and AOE and BA represent respectively allyloxyethanol and benzyl alcohol.

The siloxanes in Table 1 above were made by the following methods:—

NS124, NS 144 and NS050 were made at a scale of about 150 g by introducing reactant (DPE or AMSD) and siloxane substrate (tetramethyldisiloxane or pre-equilibrated tetramethyldisiloxane, pentamethyltrisiloxane and hexamethyltetrasiloxane with n=1 or 1.3) at a mole ratio of 55:58 reactant: Si—H bonds into a clean dry flask providing a nitrogen blanket and fitted with agitator, water condenser, and thermocouple together with a platinum complex providing a Pt concentration of 25 ppm. The reaction mixture was heated to slight reflux at about 100° C. for 2-3 hours, and the temperature then increased to 128° C. for a further 24 hours yielding a product have a small residual reactant content.

NS053, NS065, NS068 and NS078 were made by a two stage process at a scale of about 720 g. In the first stage, DPE (500 g, 2.77 moles) and tetramethyldisiloxane (200 g, 1.49 moles) were introduced into a clean dry flask providing a nitrogen blanket and fitted with agitator, water condenser, and thermocouple, warmed to 35° C. and a platinum complex introduced to provide a Pt concentration of 25 ppm. The mixture was slowly heated over about 60 minutes until reflux was achieved at 88° C., and the temperature slowly rose to 105° C. over the next 4 hours. After a further 2-3 hours, the reaction temperature was raised to and maintained at 125° C. for a further 16 to 24 hours, whereupon the second stage was carried out in which a capping reagent (0.085 moles, AMDS, AEO or BA) was introduced and the reaction continued for a further 16 to 24 hours.

NS070 was made by introducing tetramethyldisiloxane (860 g, 2.89 moles) and AMSD (220 g, 1.38 moles) introduced into a clean dry flask providing a nitrogen blanket and fitted with agitator, water condenser, and thermocouple, together with a platinum catalyst at a PT concentration of 50 ppm. The mixture was heated slowly to 85° C. when refluxing commenced and during the next hours, the temperature reaching 108° C. The temperature was maintained for a further 24 hours, whereupon further catalyst (5 ppm as Pt) was introduced and the reaction continued at 120° C. for a further 24 hours.

Herein, the refractive index of respective materials were measured at room temperature (23° C.) unless otherwise stated, employing a Becke line test (a standard procedure) for the antiperspirant active and an RFM340™ refractometer from Bellingham and Stanley Ltd for the new siloxane (NS) fluids. Each NS fluid was diluted with a diluent, either DC245 [RI=1.400] or Fluid AP [RI=1.447], in predetermined weight ratios, the refractive index of each mixture was measured and plotted against the weight proportion of the NS fluid. The refractive index of 100% NS fluid was determined by extrapolation.

Other materials employed were as follows:—

TABLE 2

| | | Brand or Supplier | Function |
|---|---|---|---|
| ISA | isostearyl alcohol | Prisorine 3515 | carrier |
| FIN | $C_{12-15}$ alkyl benzoate | Finsolve TN Fintex Inc | carrier |
| CS1 | alkylphenyl-siloxane | DC704 Dow Corning Inc | carrier |
| CS2 | cyclomethicone D5 | DC245 Dow Corning Inc | carrier |
| AACH | activated aluminium chlorohydrate RI = 1.530 | A418 Summit | Antiperspirant active |
| G1 | dextrin palmitate | Chiba | thickener |
| G2 | aspartame ester | in-house | gellant |
| G3 | N-Lauroyl-L-glutamic acid di-n-butylamide | GP-1 Ajinomoto | gellant |

Gellant G2 is the aspartame ester of Ex 1.2 in GB Patent Application No 0201164.1 in the name of Unilever plc, the PCT equivalent of which is now published as WO03/59307. Its description on page 43 and the preparative process therefor given on page 41 line 5 to 43 line 5 of WO03/59307 is specifically incorporated herein.

Example 1

In this Example, gels were made of the siloxane fluids listed in Table 1 in the absence of an antiperspirant salt to identify whether the fluid was intrinsically suited as a carrier fluid for an antiperspirant composition.

The gels were prepared in 30 ml clear glass bottles. The solvent and gelling agent were weighed directly into the bottle to give a total mixture weight of 10 g. A small Teflon stirrer bar was placed in the bottle and the mixture stirred and heated until the cyclo dipeptide had dissolved. The bottle was then removed from the heat and the solution allowed to cool and gel under quiescent conditions.

The gelling temperature of the carrier/mixture was determined by first preparing a solution of the structurant in the carrier/mixture in glass tubes, having a diameter of 20 mm and equipped with a glass thermometer resting on the bottom of the tube, in accordance with the description for Example 1 herein, and thereafter permitting the resultant solution in the tubes to cool naturally under quiescent conditions, ie without any cooling air being blown over the tubes and without the solution being stirred. External laboratory air temperature was about 23° C. Periodically, the thermometer was lifted by a few mm and if liquid had not flowed to fill the void under gravity, was carefully replaced on the tube bottom. The solution was considered to have formed a gel when it did not flow underneath the thermometer.

The gel hardness was determined by a skilled assessor of gels using a qualitative assessment by comparison with standard gels on the day after preparation. The clarity was determined by visual assessment by comparison with in-house standards.

acceptable temperatures for pouring them compared with a corresponding composition in a commercially available phenylmetylsiloxane carrier. The carrier employed in Examples

TABLE 3

| Solvent System | | | | | | | | |
|---|---|---|---|---|---|---|---|---|
| Siloxane | | Co-carrier | | Gellant | | | | |
| type | % w/w | type | % w/w | type | % w/w | Tg ° C. | Clarity | Hardness |
| NS124 | 75 | ISA | 25 | G2 | 1.5 | 25 | Clear | Medium |
| NS124 | 100 | | | 25G252 | 1.5 | 33 | Clear | Medium |
| NS053 | 75 | ISA | 25 | G2 | 1.5 | 36 | Clear | Hard |
| NS053 | 75 | ISA | 25 | G3 | 5 | 37 | Clear | Medium |
| NS078 | 75 | ISA | 25 | G2 | 1.5 | 30 | Clear | Hard |
| NS065 | 75 | ISA | 25 | G2 | 1.5 | 34 | Clear | Hard |
| NS065 | 100 | | | G2 | 1.5 | 55 | Clear | Hard |
| NS068 | 75 | ISA | 25 | G2 | 1.5 | 33 | Clear | Hard |
| NS070 | 75 | ISA | 25 | G2 | 1.5 | 60 | Clear | Hard |
| NS070 | 75 | ISA | 25 | G3 | 5 | 50 | Clear | Hard |
| NS050 | 75 | ISA | 25 | G2 | 1.5 | 53 | Clear | Hard |
| NS050 | 75 | ISA | 25 | G3 | 5 | 48 | Clear | Hard |
| Comparative data | | | | | | | | |
| CS1 | 75 | ISA | 25 | G2 | 1.5 | 58 | Clear | Hard |
| CS1 | 100 | | | G2 | 1.5 | 98 | Clear | Hard |
| CS1 | 75 | ISA | 25 | G3 | 5 | 52 | Clear | Medium |

Tg - Quiescent gelling temperature

From Table 3, it can be seen that gels of similar clarity and hardness were obtainable of the new carrier siloxanes and that some of them also had the advantage of a significantly lower gelling temperature. Consequently, they were well suited to acting as a carrier for antiperspirant actives.

Example 2

In this Example, sticks were made in a conventional manner by dissolving the structurant combination in the carrier fluids shown in Table 4 at an elevated temperature, the particulate antiperspirant active was mixed in and the composition allowed to cool and stirred. The temperature ($T_{pr}$) was noted at which the composition appeared to be on the point of gelling, but was still capable of being poured without solidifying during the pouring process.

TABLE 4

| | Ex/Comp | | | | |
|---|---|---|---|---|---|
| | 2.1 | 2.2 | 2.3 | 2.4 | C1 |
| G2 | 1.5 | 1.5 | 1.5 | 1.5 | 1.5 |
| G3 | 4.0 | 4.0 | 4.0 | 4.0 | 4.0 |
| ISA | 18.86 | 17.38 | 17.38 | 11.09 | 17.36 |
| NS053 | 49.64 | | | | |
| NS065 | | | 52.12 | | |
| NS068 | | 52.12 | | | |
| NS070 | | | | 58.41 | |
| CS1 | | | | | 52.14 |
| AACH | 25.0 | 25.0 | 25.0 | 25.0 | 25.0 |
| Fragrance | 1.0 | | | | |
| Properties | | | | | |
| $T_{pr}$ (° C.) | 65 | 67 | 69 | 87 | 85 |
| Hardness (mm) | 12.1 | 15.0 | 13.3 | 11.1 | 13.1 |
| Clarity (% T) | 5.9 | 15.8 | 7.2 | 7.3 | 15.4 |

None of Example sticks Ex2.1 to 2.4 left a white residue when applied to skin or to clothes.

From Table 4 it can be seen that the compositions according to the present invention showed an improvement in 2.1 to 2.3 respectively have similar refractive index to that in Comparison C1, but manifestly have a lower poring temperature, offering greater processing freedom for a manufacturer. Even Example 2.4 shows an advantage if like for like were compared, because it was able to be poured at substantially the same temperature as C1, even though it contained less than ⅔rds as much isostearyl alcohol, a co-carrier which in fact lowers the pour temperature for compositions containing gellants G2 and G3.

The hardness and rigidity of the composition in Example 2 were measured by penetrometry. The procedure utilises a lab plant PNT penetrometer equipped with a Seta wax needle (weight 2.5 grams) which has a cone angle at the point of the needle specified to be 9°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

The clarity of a composition (% T) was measured by placing a sample of standardised thickness in the light path of a spectrophotometer and measuring transmittance, as a percentage of light transmitted in the absence of the gel.

This test was carried out using a dual-beam Perkin Elmer Lambda 40 spectrophotometer. The sample of composition was poured hot into a 4.5 ml cuvette made of poly(methylmethacrylate) (PMMA) and allowed to cool to an ambient temperature of 20-25° C. Such a cuvette gives a 1 cm thickness of composition. Measurement was carried out at 580 nm, with an identical but empty cuvette in the reference beam of the spectrophotometer, after the sample in the cuvette had been held for 24 hours. A transmittance measured at any temperature in the range from 20-25° C. is usually adequately accurate, but measurement is made at 22° C. if more precision is required.

Example 3

In this Example, soft solid compositions can be made by dissolving the thickener in the mixture of carrier fluids at an elevated temperature, 110° C., cooling the resultant solution to 80-85° C., stirring in the particulate AACH and when the composition has reached about 65° C., pouring it into a soft solid barrel having at its dispensing end a plurality of slits having a minor axis diameter of 3 mm. A sample is also poured into a 5 cm cuvette to enable its light transmission to be measured.

TABLE 5

|  | Ex/Comp | |
|---|---|---|
|  | 3.1 | 3.2 |
| G1 | 10 | 10 |
| Fin | 30 | 3.25 |
| NS078 | 35 | 48.75 |
| CS2 |  | 13.0 |
| AACH | 25 | 25 |

In the formulations summarised in Table 5, the RI of the carrier oils and the antiperspirant active were designed to differ by 0.004. As a consequence, the formulations in bulk are opaque, having a % T of <1%, but the ribbons of soft solid that are extruded through the dispensing apertures are translucent.

The products leave no significant visible white deposits when applied to skin or clothes.

The use of high RI silicone oils in accordance with the present invention enables the formulator to retain the sensory benefits arising from employing a siloxane oil as the main carrier for a similar extent of RI matching. It can also permit a significant fraction of a cyclomethicone to be employed, as in Example 3.2.

The invention claimed is:

1. An anhydrous antiperspirant composition comprising
   a) from 0.5 to 50% by weight of a particulate aluminium and/or aluminium/zirconium antiperspirant active;
   b) from 30 to 95% by weight of a water-immiscible carrier fluid or mixture of carrier fluids; and
   c) from 0.1 to 40% by weight of a thickener, gellant or structurant for the carrier fluid;
in which the carrier fluid comprises an aryl substituted siloxane which satisfies the general formula 1

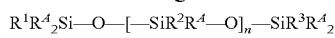

in which:
   n represents an average number of from 0 to 2;
   $R^1$ $R^2$ and $R^3$, which may be the same as or different from each other, each represents $R^4$ or a capping group $R^C$, wherein:
      $R^4$ represents diphenylethyl, and
      $R^C$ represents a residue of α-methylstyrene dimer, benzyl alcohol or allyloxy ethanol,
   with the proviso that not more than 20% of the total occurrences of —$R^1$, $R^2$ and $R^3$ are $R^C$, and $R^A$ represents a methyl group;
and wherein at least 30% by weight of the carrier fluid or mixture of carrier fluids is the aryl substituted siloxane, and wherein the anhydrous antiperspirant composition is in the form of a cream, soft solid or stick.

2. A composition according to claim 1 in which $R^4$ represents a mixture of diphenylethyl and the hydrogenated residue of x-methylstyrene dimer.

3. A composition according to claim 1 wherein $R^C$ is the residue of α-methylstyrene dimer.

4. A composition according to claim 1 in which $R^C$ represents a residue of benzyl alcohol or allyloxy ethanol.

5. A composition according to claim 1 at least 85% of the total occurrences of $R^1$, $R^2$, and $R^3$ are diphenylethyl.

6. A composition according to claim 1 in which n is from 0 to 1.5.

7. A composition according to claim 1 in which n is 0.

8. A composition according to claim 4 in which the proportion of diphenylethyl group is from 85 to 90%.

9. A composition according to claim 1 in which $R^4$ represents the residue of α-methylstyrene dimer.

10. A composition according to claim 9 in which n in the formula is 1+/−0.2.

11. A composition according to claim 1 in which at least 50% by weight of the carrier fluid or mixture of carrier fluids is the aryl substituted siloxane.

12. A composition according to claim 11 in which from 60 to 90% by weight of the mixture of carrier fluids is the aryl substituted siloxane.

13. A composition according to claim 1 in which the mixture of carrier fluids comprises one or more water-immiscible fluids selected from volatile polycyclomethicone or linear polymethicone oils, non-volatile polymethicone oils, liquid branched aliphatic alcohol, liquid alkyl benzoate esters and liquid polyalkylene glycol ethers.

14. A composition according to claim 13 in which the mixture of carrier fluids comprises the aryl substituted siloxane fluid and the liquid branched aliphatic alcohol in a weight ratio of from 6:1 to 2:1.

15. A composition according to claim 1 in which the carrier fluid and suspended antiperspirant active have refractive index matching within 0.005 units.

16. A composition according to claim 1 in which the antiperspirant active is selected from aluminium chlorohydrate or activated aluminium chlorohydrate.

17. A composition according to claim 1 in which the antiperspirant active is selected from aluminium/zirconium chlorohydrate and complexes of aluminium/zirconium chlorohydrate with an amino acid.

18. A composition according to claim 17 in which the antiperspirant active is a complex of aluminium/zirconium chlorohydrate and glycine.

19. A composition according to claim 1 in which the carrier fluid is thickened or solidified with an effective amount of a structurant comprising a silicone-oil-soluble polymeric gellant or non-polymeric fibre-forming gellant.

20. A composition according to claim 19 in which the polymeric gellant comprises a polyalkylene, a polyalkylene/polyarylene block copolymer a polyamide or a polyamide/polysiloxane copolymer.

21. A composition according to claim 19 in which the non-polymeric fibre-forming gellant is selected from cellobiose esters, lanosterol, a combination of a sterol and a sterol ester, hydroxystearic acid, N-acyl amino acid amides and esters, diamido derivatives of cyclohexane, amido derivatives of aliphatic di or tri-carboxylic acids, and cyclic derivatives of aspartame.

22. A composition according to claim 1 in which the proportion of structurant is selected in the range of from 2 to 15% by weight.

23. A composition according to claim 1 in which the composition is in the form of a stick that has a hardness of greater than 0.5 N/mm$^2$ by sphere indentation.

* * * * *